United States Patent [19]

Miyachi et al.

[11] 4,398,023
[45] Aug. 9, 1983

[54] β-1,3-GLUCANPOLYOL, PROCESS FOR PREPARATION THEREOF, AND UTILIZATION THEREOF

[75] Inventors: Hideki Miyachi, Inazawa; Akira Misaki, Nishinomiya; Mariko Kakuta, Tanabenishino; Mineo Nakayama, Hachioji; Hideo Nagae, Kasugai, all of Japan

[73] Assignee: Meito Sangyo Kabushiki Kaisha, Nagoya, Japan

[21] Appl. No.: 182,617

[22] Filed: Aug. 29, 1980

[30] Foreign Application Priority Data

Aug. 29, 1979 [JP] Japan .................... 54-109015

[51] Int. Cl.$^3$ ............................... C08B 37/00
[52] U.S. Cl. .................... 536/1.1; 424/180; 536/124; 536/4.1; 536/120
[58] Field of Search ............ 424/180; 536/1, 4, 1.1, 536/4.1, 120

[56] References Cited

U.S. PATENT DOCUMENTS

| | | | |
|---|---|---|---|
| 3,301,848 | 1/1967 | Halleck ................................ | 536/1 |
| 3,396,082 | 8/1968 | Davis et al. .......................... | 536/1 |
| 3,632,802 | 1/1972 | BeMiller et al. ..................... | 536/1 |
| 3,754,925 | 8/1973 | Kimura et al. ....................... | 536/1 |
| 3,822,250 | 7/1974 | Kimura et al. ....................... | 536/1 |
| 3,856,775 | 12/1974 | Fukuoka et al. ..................... | 536/1 |

FOREIGN PATENT DOCUMENTS 55-25409 2/1980 Japan .

OTHER PUBLICATIONS

Seikagaku, vol. 50, No. 9, p. 767 (1978).
Seikagaku, vol. 51, No. 8, p. 616 (1979).
Agricultural and Biological Chemistry 42 (2), 417–425 (1978).

*Primary Examiner*—Johnnie R. Brown
*Attorney, Agent, or Firm*—Wenderoth, Lind & Ponack

[57] ABSTRACT

β-1,3-glucanpolyol derived from β-1,3-glucan produced by a β-1,3-glucan-producing strain of the genus Pestalotia, said glucanpolyol having an intrinsic viscosity [η] of about 1 to about 10 and comprising a main chain having as repeating units β-1,3-glucopyranose units of the following formula →3) β-D-Glc (1→ wherein Glc represents a glucopyranose residual moiety, and bonded thereto, either side chains of formula (B), or both side chains of formulas (A) and (B) below

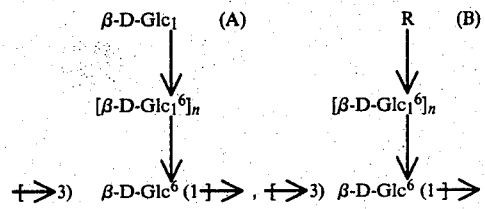

wherein n represents a number of from 0 to 1, and →3) β-D-Glc (1→ represents the above main chain, and R represents a group derived from β-D-glucopyranose of the formula

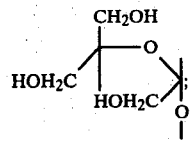

a process for production thereof, and its pharmaceutical use.

1 Claim, 2 Drawing Figures

FIG. I

FIG. 2

β-1,3-GLUCANPOLYOL, PROCESS FOR PREPARATION THEREOF, AND UTILIZATION THEREOF

This invention relates to novel β-1,3-glucanpolyol derived from β-1,3-glucan produced by a β-1,3-glucan-producing strain belonging to the genus Pestalotia, a process for production thereof, and to a pharmaceutical composition comprising the β-1,3-glucanpolyol as an active ingredient. The β-1,3-glucanpolyol has low toxicity and exhibits antitumor activity.

More specifically, this invention relates to β-1,3-glucanpolyol having the following characteristics [I] and [II] and derived from β-1,3-glucan produced by a β-1,3-glucan-producing strain belonging to the genus Pestalotia, a process for production thereof, and to a pharmaceutical composition comprising the β-1,3-glucanpolyol as an active ingredient.

[I] The β-1,3-glucanpolyol comprises a main chain having as repeating units β-1,3-glucopyranose units of the following formula wherein Glc represents a glucopyranose residual moiety,
and bonded to the main chain, either side chains of the following formula (B) or side chains of the following formulas (A) and (B)

wherein n represents a number of from 0 to 1, and $\rightarrow$) β-DGlc (1$\rightarrow$ represents the aforesaid main chain, wherein n and $\rightarrow$3) β-D-Glc (1$\rightarrow$ are as defined above with respect to formula (A), and R is a group derived from β-D-glucopyranose of the formula (to be sometimes referred to as a polyalcohol residue).

[II] The β-1,3-glucanpolyol has an intrinsic viscosity [η] of about 1 to about 10.

Preferably, in the above β-1,3-glucanpolyol, the number of the side chains of formula (B) is about 25 to about 70 per 100 β-1,3-glucopyranose units of the main chain $\rightarrow$3) -D-Glc (1$\rightarrow$, and the number of the side chains of formula (A) is 0 to about 45 on the same basis.

According to this invention, the β-1,3-glucanpolyol can be obtained by subjecting β-1,3-glucan produced by a β-1,3-glucan-producing strain of the genus Pestalotia, for example Pestalotia No. 815 strain (FERM-P No. 5147) to an oxidation treatment with periodic acid or its water-soluble salt and then subjecting it to a reducing treatment, and if desired, subjecting it to a treatment of reducing its viscosity in any desired stage in this process.

The starting β-1,3-glucan does not have the side chain of formula (B) and comprises a main chain having as repeating units β-1,3-glucopyranose units of the formula wherein Glc represents a glucopyranose residue, and bonded to the main chain, side chains of the following formula (A)

wherein n represents a positive number of from 0 to 1, and $\rightarrow$3) β-D-Glc$\rightarrow$represents the aforesaid main chain.

Preferably, the number of the side chains of formula (A) in the β-1,3-glucan is about 55 to about 75 per 100 β-1,3-glucopyranose units in the main chain, and the number of the side chains corresponding to n=1 is about 2 to about 8 per 100 said units.

It has been known that polysaccharides having antitumor activities are found in polysaccharides obtained from extracts of fruit bodies of Basidiomycetes or from mycelia or culture broths of Basidiomycetes, yeasts and other microorganisms, for example glucans, mucopolysaccharides and lipopolysaccharides. However, because their antitumor activities are not sufficient for practical application or have a narrow antitumor spectrum, these polysaccharides have only limited clinical application.

SEIKAGAKU, Vol. 50, No. 9, page 767, 1978 (published by the Japanese Biochemical Society on Sept. 25, 1978) reported that acidic polysaccharides and water-soluble gulcan and hot alkali-insoluble glucan were obtained from the fruit body of *Auricularia auricula-judae* and the water-soluble glucan showed a strong inhibitory action on Sarcoma 180 transplanted in mice, and describes the results of analysis of these polysaccharides. A similar report was made in SEIKAGAKU, Vol. 51, No. 8, page 616, 1979 (published in the Japanese Biochemical Society on Aug. 25, 1979).

Prior to these reports, some of the inventors of the present application, based on the report made in Agricultural and Biological Chemistry 42 (2), 417–425, 1978, filed a patent application relating to a process for producing β-1,3-glucanpolyol having an intrinsic viscosity [η] of about 15 to about 30 which comprises extracting the fruit body or mycelium of a strain belonging to the genus Auricularia with an aqueous medium under alkaline conditions, collecting the insoluble portion, subjecting it to an oxidation treatment with periodic acid or its water-soluble salt, and then subjecting it to a reducing treatment; the resulting β-1,3-glucanpolyol; and a tumor treating agent comprising the resulting β-1,3-glucanpolyol (Japanese Patent Application No. 97285/78 laid-open on Feb. 23, 1980 under Laid-Open Patent Publication No. 25409/80).

The present inventors made investigations in order to provide glucanpolyol having a broader spectrum of antitumor activity. These investigations have led to the discovery that β-1,3-glucanpolyol having the aforesaid characteristics [I] and [II] which has not been proposed heretofore can be produced by a similar technique to that in the aforesaid prior application from a novel starting β-1,3-glucan produced by a β-1,3-glucan-producing strain of the genus Pestalotia. The β-1,3-glucanpolyol is characterized by having an intrinsic viscosity [η] of about 1 to about 10 which is much lower than that of the polyol disclosed in the prior application.

The inventors have also found that the β-1,3-glucanpolyol having the aforesaid characteristics [I] and [II] is a novel glucanpolyol which shows a much wider antitumor spectrum than known polysaccharides having antitumor activities, has low toxicity, contains the alcohol residue R in formula (B) (which is not present in the untreated β-1,3-glucan) in its side-chain section, and has two clear absorption bands in the vicinity of 2900 cm$^{-1}$ in its infrared absorption spectrum, which do not exist in the infrared absorption spectrum of the untreated β-1,3-glucan.

It is an object of this invention to provide novel β-1,3-glucanpolyol having a much broader antitumor spectrum than known polysaccharides having antitumor activities.

Another object of this invention is to provide a process for producing the novel β-1,3-glucanpolyol easily in good yields from the β-1,3-glucan which is produced by a β-1,3-glucan-producing strain belonging to the genus Pestalotia.

Still another object of this invention is to provide a tumor treating agent comprising the novel β-1,3-glucanpolyol as an active ingredient.

The above and other objects and advantages of this invention will become more apparent from the following description.

The properties and structure of the β-1,3-glucanpolyol of this invention are summarized below.

Homogenity

It shows a single peak in a uniformity test conducted by an ultracentrifugal analysis.

Specifically, it shows a single spot in electrophoresis using a sodium borate buffer (pH=9.3) as a solvent system. Thus, the β-1,3-glucan of this invention is determined to be a homogenity substance.

Solubility

Soluble at room temperature in water, a 1 N aqueous solution of sodium hydroxide, dimethyl sulfoxide, etc. (frequently forms a sol-like solution having high flowability). Insoluble or sparingly soluble at room temperature in alcohols, acetone, ethers, etc.

Intrinsic viscosity

The intrinsic viscosity of the β-1,3-glucanpolyol of this invention is usually about 1 to about 10 although it slightly differs depending upon the degree of oxidation with periodic acid or its water-soluble salt in the manufacturing process and upon the presence or absence of the treatment of viscosity decreasing and the degree of the treatment, etc.

The intrinsic viscosity, as used in the present invention, is [η] defined by the following equation.

$$[\eta] = \lim_{C \to 0} \eta_{sp}/C$$

wherein $\eta_{sp} = (\eta - \eta_o)/\eta_o = \eta/\eta_o - 1$ in which η is the viscosity (at 25° C. in aqueous solution) of the solution and $\eta_o$ is the viscosity of the solvent; and C is the concentration in g/100 ml.

Infrared absorption spectrum

Figure 1:
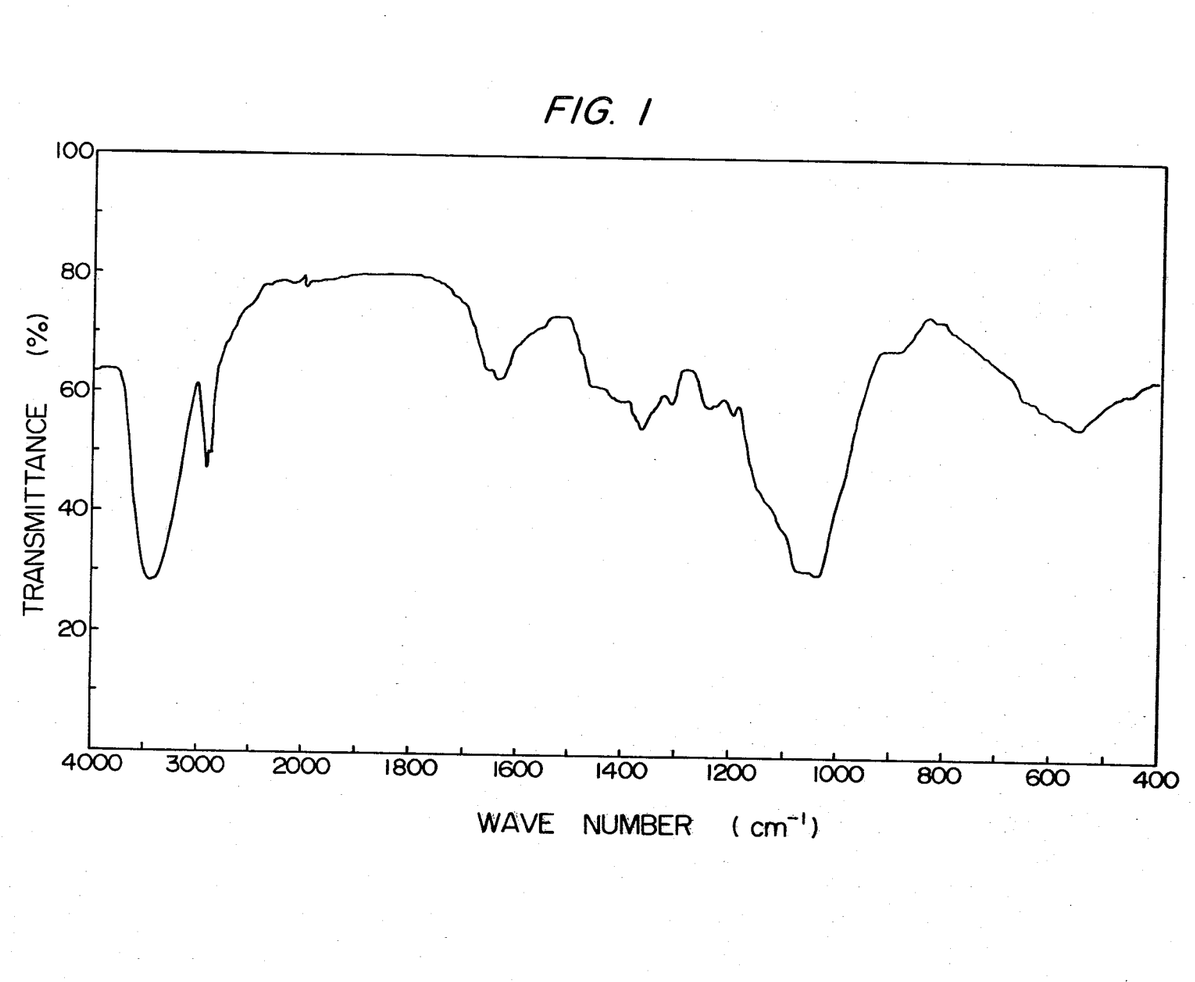
Figure 2:
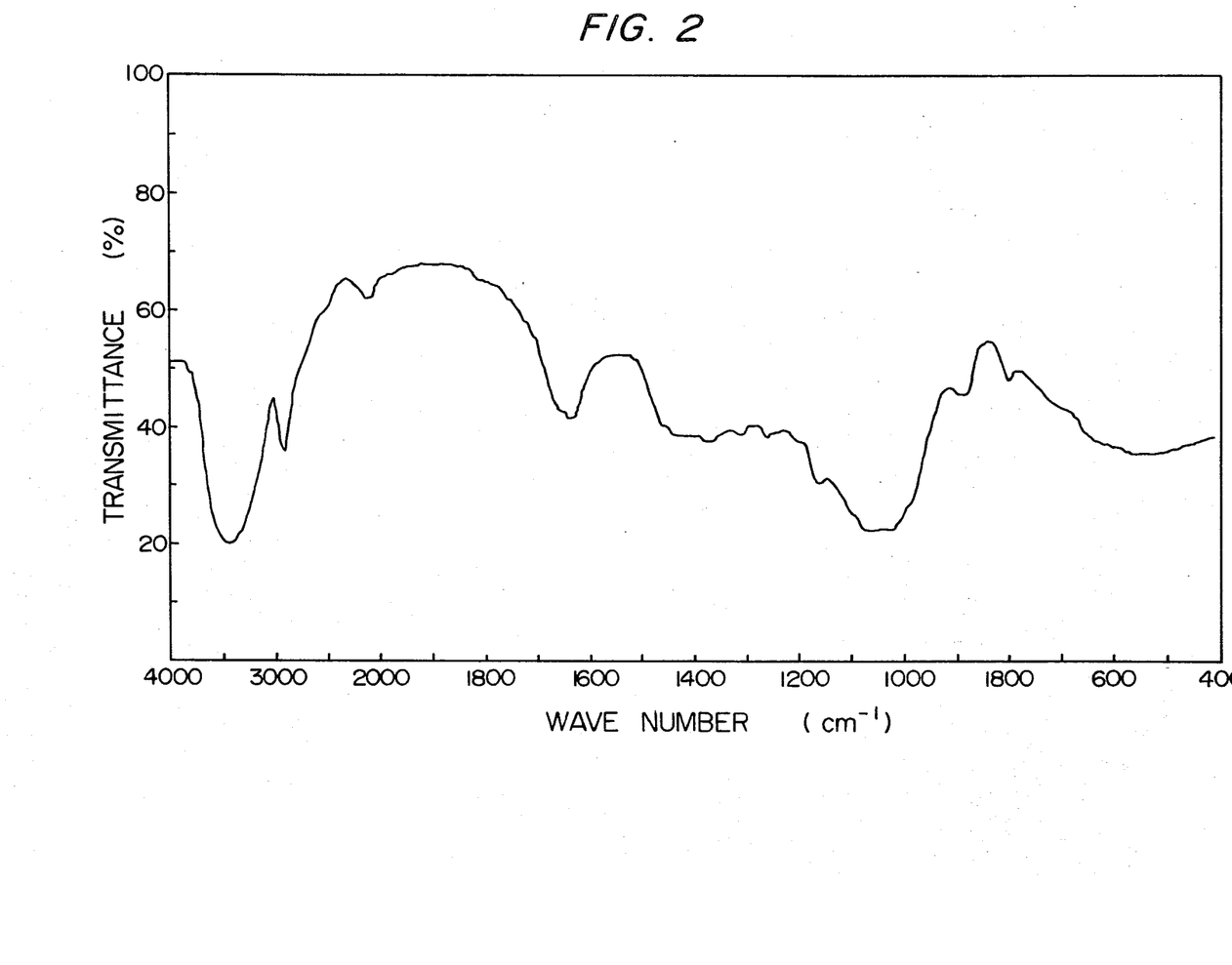

Two clear absorptions exist in the vicinity of 2900 cm$^{-1}$. These absorptions are different from the broad absorption of the starting β-1,3-glucan.

FIG. 1 of the accompanying drawings shows an infrared absorption spectrum (KBr tablet method) of the β-1,3-glucanpolyol obtained in Example 1 to be given hereinbelow, and FIG. 2 shows an infrared absorption spectrum of the starting β-1,3-glucan.

Component sugars

The products obtained by complete hydrolysis of β-1,3-glucanpolyol with ordinary inorganic acids or organic acids have been determined to be D-glucose, glycerol and glycolaldehyde by paper chromatography [solvent system: butanol/pyridine/water (6:4:3); spray reagent, a silver nitrate solution].

Glucose and glycerol are determined as alditol acetate by gas chromatography.

Structure (A) When the glycanpolyol of this invention is completely oxidized with 0.05 N periodic acid, 0 to 0.52 mole, based on the constituent sugar residues, of periodate is consumed, and simultaneously, production of 0 to 0.26 mole of formic acid is ascertained.

(B) When the glucanpolyol of this invention is reduced with sodium borohydride and then completely hydrolyzed with an acid, glucose alone or both glucose and small amounts of glycerol and glycolaldehyde are formed as decomposition products.

(C) When the glucanpolyol of this invention is oxidized with periodic acid and then reduced with sodium borohydride and then hydrolyzed with an acid under mild conditions, a water-soluble polymeric glucan composed only of β-(1→3)-D-glucoside linkages is formed, and in its water-soluble portion, no decomposition product is noted or the presence of only a small amount of glycerol is ascertained. In either case, glycerol-D-glucoside is not detected.

(D) When the water-insoluble glucan described in (C) above is methylated and hydrolyzed and the methyl sugars are converted into alditol acetate and subjected to gas-chromatographic analysis, only 2,4,6-tri-O-methyl-1,3,5-tri-O-acetyl-D-glucitol and a trace of 2,3,4,6-tetra-O-methyl-1,5-di-O-acetyl-D-glucitol are formed.

(E) When the glucanpolyol of this invention is methylated and hydrolyzed and then the methyl sugars are converted into alditol acetate and subjected to gas-chromatographic analysis, 2,4,6-tri-O-methyl-1,3,5-tri-O-acetyl-D-glucitol and 2,4-di-O-methyl-1,3,5,6-tetra- O-acetyl-D-glucitol and highly volatile 1,3-di-O-methyl-2-O-acetyl-glycerol are separated and identified as main components. Small amounts of 2,3,4,6-tetra-O-methyl-1,5-di-O-acetyl-glucitol and 2,3,4-tri-O-methyl-1,5,6-tri-O-acetyl-D-glucitol are separated and identified, or are not at all formed.

It is seen from the results obtained that the novel β-1,3-glucanpolyol of this invention is a polysaccharide composed of glucose and the polyalcohol residue R in formula (B), in which the side chains of formula (B) or both formula (B) and (A) are attached to the glucopyranose residue forming the glucan main chain of the β-(1→3) linkage. It will be readily appreciated that if n is 1 in formula (B), the β-D-glucopyranose with n can also be of the structure represented by R, and the formula (B) is meant to include this case. In the glucanpolyol of this invention, a residue of a lower carbon number resulting from hydrolysis of the 5-carbon polyalcohol residue of formula R could exist together. This case is also included within the scope of this invention.

The proportion of the side chains of formula (A), based on the β-(1→3) glucopyranose units of the main chain, in the β-1,3-glucanpolyol of this invention can be calculated from the amount of periodic acid consumed in the experiment shown in (A) above with regard to its structure. The proportion of the side chains of formula (B) can be calculated from the mole ratios of glycerol and glycose in the experiment conducted and described above for the component sugars.

The proportions of the side chains of formulas (A) and (B) can also be calculated from the proportions of 2,3,4,6-tetra-O-methyl-1,5-di-O-acetyl-D-glucitol, 2,4,6-tri-O-methyl-1,3,5-tri-O-acetyl-D-glucitol, 2,3,4-tri-O-methyl-1,5,6-tri-O-acetyl-D-glucitol, 2,4-di-O-methyl-1,3,5,6-tetra-O-acetyl-D-glucitol, and 1,3-di-O-methyl-2-O-acetyl-glycerol.

The β-1,3-glucan used in the production of β-1,3-glucanpolyol of this invention can be obtained by cultivating a β-1,3-glucan-producing strain of the genus Pestalotia, and recovering the product from the culture broth.

An example of the β-1,3-glucan-producing strain is Pestalotia No. 815 (e.g., FERM-P No. 5147 strain; ATTC No. 20604)

The microbiological properties of Pestalotia No. 815 are as follows:

Cultural characteristics

Colonies on potato glucose agar, rapid, spreading, white, later becoming grayish-brown; aerial hyphae, scanty, dense in center, sparse in marginal area. Acervuli develop at maturity. Conidia scattered or agglutinated in a greenish-black mass as acervuli develop. Reverse almost colorless.

Microscopic observations

Aerial hyphae, hyaline, irregularly branched, 2–3μ wide. Conidiophores, long cylindrical, 10–20μ (sometimes 30μ) long, aseptate, 2–3.5μ wide, annellated. Conidia, thallic, of aleurioconidia-type, clavate, fusoid, four-septate (five cells), with hyaline, pointed end cells, 18–25μ×5–6μ. Apical appendages, long, two or three in number, 15–30μ (sometimes 50μ) long; basal appendage, single, straight, 6–10μ long. Median three cells, faint brown, constricted at the septa. Conidia produced from conidiophores with annellation.

Taxonomical position

A study of the above cultural characteristics and microscopic observations with reference to "Ainsworth and Bisby's Dictionary of the Fungi", sixth edition: Commonwealth Mycological Institute, Kew, Surrey, England (1971) has led to identification of this microorganism as one of the species of Deuteromycotina (subdivision), Coelomycetes (class), Melanconiales (order), Pestalotia (genus).

The starting β-1,3-glucan used in this invention can be produced by cultivating the aforesaid β-1,3-glucan-producing strain of the genus Pestalotia, removing the mycelia from the culture broth, adding methanol, ethanol, acetone, etc. to precipitate the crude glucan, and if desired, purifying the crude glucan and then recovering the purified glucan.

The cultivation is carried out under aerobic conditions in a culture medium containing suitable carbon sources and preferably further containing suitable nitrogen sources and minerals. Examples of the carbon sources are glucose, mannose, fructose, sorbose, sucrose, maltose, and mannitol. Examples of the nitrogen sources include organic nitrogen sources such as peptone, yeast extract, corn steep liquor and defatted soybean flour and inorganic nitrogen sources such as ammonium sulfate and ammonium nitrate. In many cases, better results are obtained by adding small amounts of minerals such as magnesium salts and phosphoric acid salts, and vitamins.

The cultivation can be carried out by using a liquid culture medium or a solid culture medium, but the use of a liquid culture medium is common. Preferably, shaking flask cultivation or an aeration-stirring means is used in liquid culture. The cultivation may be carried out at about 10° to about 40° C., preferably about 20° to about 35° C., at a pH of about 4 to about 9, preferably about 5 to about 8. The cultivation can be performed, for example, for about 1 to about 7 days.

After the cultivation, the liquid phase or the cultivation mixture is separated into mycelia and a cultivation filtrate by such means as filtration or centrifugal separation. If desired, the mycelia are washed with water several times, and the wash liquids are combined with the cultivation filtrate. When a suitable precipitant, for example a water-miscible solvent such as methanol, ethanol, isopropanol or acetone, is added to the combined mixture in an amount about 1 to about 4 times the volume of the former. Thus, the crude glucan is obtained as a precipitate.

This crude glucan may be used as a starting material immediately then, or after it is dried at a low temperature. If desired, it may be further treated prior to use.

For example, the starting crude glucan is stirred in about 100 to 200 times its amount of an aqueous sodium chloride solution, for example an aqueous sodium chloride solution having a concentration of about 0.5 to 1.0%, if desired at an elevated temperature of about 90° to about 95° C., for about 30 minutes to about 1 hour. The treated glucan is centrifuged to remove the liquid layer. An alkaline aqueous solution, for example, an about 0.1–1.0 N aqueous solution of sodium hydroxide is added to the residue in an amount about 100 to about 200 times the amount of the latter, and then the mixture is centrifuged. The liquid layer is neutralized with an acid such as hydrochloric acid, and a precipitant such as methanol, ethanol or acetone is added in an amount about 1 to about 4 times the former. The precipitate is then separated and collected. This treatment procedure is repeated a suitable number of times. Then, if desired, proteins and other impurities are removed by gel filtration, dialysis, etc. The precipitate is suspended in about 50 to 100 times its weight of distilled water. The suspension is fully stirred, and the aforesaid precipitant is added to form a precipitate which is separated and collected. It is then dried, for example at low temperature and reduced pressure, to afford the starting β-1,3-glucan.

The β-1,3-glucan is then oxidized in accordance with this invention with periodic acid or its water-soluble salt. In performing the oxidation treatment, 1 part of the starting glucan is suspended or dissolved in about 50 to about 500 parts of an aqueous solution containing periodic acid or its water-soluble salts (e.g., sodium metaperiodate or potassium metaperiodate) having a concentration of about 0.01 to about 0.5, preferably about 0.05 to about 0.2 M, and if required a buffer, such as an acetate buffer or citrate buffer, usually used at a pH of 3 to 8. The suspension or solution is stirred to react them with each other. The proportion of the periodic acid or its water-soluble salt based on the starting glucan is not particularly restricted, but favorable results can be obtained when using about 0.1 to about 3 moles of the starting glucan based on the anhydrous glucose units.

Preferably, the reaction operation is carried out in a dark place at as low a temperature as possible, usually at room temperature or below, preferably below about 15° C., more preferably below about 5° C. The reaction time is about 2 to about 10 days, desirably about 2 to about 5 days. In this case, more favorable results can be obtained by optionally sampling the reaction mixture, examining the amount of periodic acid consumed by the Fleury-Lange method (J. Pharm. Chem. 17, 196, 1933) to determine the degree of oxidation and the occurrence of peroxidation reaction as a side-reaction, and controlling the reaction such that the desired oxidation can be performed.

The reducing treatment after the oxidation reaction may be carried out by separating the resulting oxidation product, adding an aqueous medium and reducing the mixture with a reducing agent; or by directly reducing the resulting oxidation product with a reducing agent without isolating it from the reaction system.

In the latter case, the oxidation product may be pretreated by, for example, decomposing the unreacted periodic acid therein with ethylene glycol, or by dialyzing it to remove the unreacted periodic acid and by-products. The reaction can be performed more effectively by adjusting the pH of the oxidation reaction mixture to a slightly alkaline region (pH about 8) with sodium bicarbonate, sodium carbonate, etc.

Preferably, the reducing agent is water-soluble. For example, palladium carbon may be used, but usually sodium borohydride ($NaBH_4$) is used. The amount of the reducing agent is about 1 mole or more preferably about 1.2 to about 2 moles, per mole of the periodic acid in the oxidation reaction. Use of an excessive amount of the reducing agent does not adversely affect the reducing reaction. It is sufficient that the reducing reaction is usually carried out for about 1 to about 2 days. If desired, the time for the reducing reaction may be shorter or longer.

After the reducing reaction, the excess of $NaBH_4$ is decomposed by adding a mineral acid such as hydrochloric acid or an organic acid such as acetic acid, and if required, the water-insoluble residue in the reaction mixture may be removed by known means such as centrifugation or filtration. Alternatively, the excess of $NaBH_4$ may be decomposed after removing the water-insoluble residue. The desired product may be obtained from the resulting water-soluble fraction by removing the by-products by known means such as dialysis, and then lyophilizing or spray drying the residue. The desired product may also be separated and recovered by adding a water-miscible non-solvent such as methanol, ethanol, isopropanol or acetone. The amount of the non-solvent added at this time may be more than the minimum amount which can induce precipitation of the final desired product. Usually, it is about 1 to about 5 times the volume of the water-soluble fraction. The precipitate is dried and if required, powderized to obtain the desired β-1,3-glucanpolyol.

If desired, the resulting β-1,3-glucanpolyol may be purified by known purifying means such as re-precipitation or dialysis.

In the practice of the process of this invention, a treatment of viscosity decreasing may be carried out at any desired stage in the process for producing the β-1,3-glucanpolyol. This treatment can bring about a further reduction in the toxicity of the product, and offer various advantages in drug formulation.

The treatment of viscosity decreasing can be performed, for example, by ultrasonic treatment, acid hydrolysis, enzymatic degradation, or addition of a hydrogen bond-cleaving agent. The treatment can be performed once or a plurality of times. These treating methods may be used singly or as a combination of two or more.

In performing the ultrasonic treatment as the treatment of viscosity reduction, an aqueous solution or aqueous suspension as the material to be treated is placed in a suitable vessel at any desired stage of the manufacturing process, and optionally with stirring, it is subjected to irradiation of ultrasonic waves. The frequency of ultrasonic waves is not particularly restricted, but usually it is about 10 kilohertz to about 500 kilohertz. The treating temperature is preferably not more than about 50° C. If desired, the treating vessel is cooled to prevent a temperature rise of the treating solution. The treating time can be selected suitably depending upon the properties of the material to be treated and those of the final desired product. Usually, a period of about 300 minutes or less is sufficient. After the ultrasonic treatment, the product may be subjected to the subsequent manufacturing operation either as such or after it is separated.

In performing the acid hydrolysis treatment as the treatment of reducing viscosity, a mineral acid such as hydrochloric or sulfuric acid or an organic acid such as formic acid is added to the aqueous solution or aqueous dispersion as the material to be treated. There is no particular restriction on the treating conditions. However, when this treatment is carried out after the completion of the reducing treatment, it is desirable from the standpoint of the yield or the antitumor effect of the final product, to employ mild conditions, for example to use about 0.01–0.2 N hydrochloric acid or sulfuric acid at as low a temperature as possible, usually at room temperature or below, preferably not more than about 15° C., for about 10 to about 24 hours. After the treatment, the product is neutralized with an alkali such as sodium hydroxide, potassium hydroxide, barium hydroxide or sodium carbonate, and subsequently, the next manufacturing operation is carried out. Or the treated product is first separated, and subjected to the aforesaid operation.

In performing the enzymatic treatment as the treatment of viscosity decreasing, a β-1,3-glycan-decomposing enzyme, such as Zymolyase 5000 (a kind of an endotype β-1,3-glucan-decomposing enzyme), is caused to act on the material to be treated in, for example, an aqueous medium at any desired stage of the manufacturing process. After the treatment, the enzyme is removed in a customary manner and then the next manufacturing operation is carried out. Alternatively, the treated product is first separated and then subjected to the above operation.

In adding a hydrogen bond cleaving agent as the treatment of viscosity decreasing, at least one compound having the property of cleaving a hydrogen bond, such as urea, guanidine or the derivatives thereof, is added to an aqueous solution or an aqueous dispersion as the material to be treated at any desired stage of the manufacturing process, and the mixture is stirred. For example, 1 to 4 parts of urea is added to 1 part of the aqueous solution which has been subjected to the reducing treatment, and the mixture is stirred at about 20° to about 100° C. for 24 hours. Urea is then removed by dialysis, etc., and then the residue is lyophilized or spray-dried to obtain the desired product. Or methanol, ethanol, or acetone is added to form a precipitate which is dried to obtain the desired product.

The resulting β-1,3-glucanpolyol of this invention derived from the starting glucan which is produced by a β-1,3-glucan-producing strain of the genus Pestalotia has an intrinsic viscosity [η] of about 1 to about 10 and comprises a main chain having as recurring units β-1,3-glucopyranose units to which are attached side chains of formula (B) or both formula (B) and (A), the number of the side chains (B) and the number of side chains (A) being about 25 to about 70, and about 0 to about 45, respectively, per 100 β-1,3-glucopyranose units of the main chain.

The proportions of the side chains and the intrinsic viscosity [η] can be varied as desired within the specified ranges by choosing the degree of oxidation in oxidizing the starting glucan with periodic acid or its water-soluble salt or the degree of reducing the viscosity in the treatment of viscosity reduction.

The antitumor activity of the β-1,3-glucanpolyol of this invention is shown by the following animal experiments.

(1) An antitumor activity test using Sarcoma 180 in ICR-JCL mice

The ascites cells of Sarcoma 180 were inoculated peritoneally in ICR-JCL mice having a body weight of about 23 g. One week later when the ascites fully increased, 6 million tumor cells of Sarcoma 180 were transplanted into the subcutaneous portion of the back of the mice through the right inguinal part. Starting 24 hours after the transplantation, the glucanpolyol of this invention was intraperitoneally administered once a day for 10 days. In the fifth week, the tumor was enucleated and its weight was compared with that in non-treated groups. The tumor inhibition ratio was calculated, and the number of tumors which completely regressed was observed.

The tumor inhibition ratio was calculated in accordance with the following equation.

$$\text{Inhibition ratio} = \frac{\overline{C} - \overline{T}}{\overline{C}} \times 100$$

wherein
$\overline{C}$ is the average weight of tumor in non-treated groups (10 mice per group),
$\overline{T}$ is the average weight of tumor in treated groups (10 mice per group).

The results are shown in Table 1.

TABLE 1

| Sample | Dosage (mg/kg/day) | Average weight of tumor (g) | Tumor inhibition ratio (%) | Complete regression |
|---|---|---|---|---|
| Product of Example 1 | 1 | 0.28 | 97.5 | 9/10 |
| Product of Example 1 | 5 | 0 | 100 | 10/10 |
| Product of Example 1 | 10 | 0.17 | 98.5 | 9/10 |
| Product of Example 2 | 5 | 0.30 | 97.3 | 8/10 |
| Product of Example 3 | 5 | 0.64 | 94.2 | 7/10 |
| Product of Example 4 | 1 | 0.92 | 91.6 | 6/10 |
| Product of Example 4 | 5 | 0.41 | 96.3 | 8/10 |
| Product of Example 5 | 1 | 1.39 | 87.4 | 6/10 |
| Product of Example 5 | 5 | 0.79 | 92.8 | 7/10 |
| Product of Example 6 | 5 | 0 | 100 | 10/10 |
| Control | | 11.01 | — | 0/10 |

(2) An antitumor activity test using Ehrlich Carcinoma in ICR-JCL mice 3.5 Million Ehrlich carcinoma cells were transplanted into the subcutaneous portion of the right inguinal part of ICR-JCL mice having a body weight of about 23 g, and subsequently, the same operation as in (1) above was performed.

The results are shown in Table 2.

TABLE 2

| Sample | Dosage (mg/kg/day) | Average weight of tumor (g) | Tumor inhibition ratio (%) | Complete regression |
|---|---|---|---|---|
| Product of Example 1 | 1 | 0 | 100 | 10/10 |
| Product of Example 1 | 5 | 0 | 100 | 10/10 |
| Product of Example 1 | 20 | 0.31 | 97.9 | 7/10 |
| Product of Example 2 | 1 | 1.27 | 91.5 | 6/10 |
| Product of Example 2 | 5 | 0.83 | 94.4 | 7/10 |
| Product of Example 3 | 1 | 1.15 | 92.3 | 7/10 |
| Product of Example 3 | 5 | 0.67 | 95.5 | 7/10 |
| Product of Example 4 | 1 | 1.48 | 90.1 | 6/10 |
| Product of Example 4 | 5 | 0.97 | 93.5 | 6/10 |
| Product of Example 5 | 1 | 1.82 | 87.8 | 4/10 |
| Product of Example 5 | 5 | 1.64 | 89.0 | 5/10 |
| Product of Example 6 | 1 | 0 | 100 | 10/10 |
| Product of Example 6 | 5 | 0 | 100 | 10/10 |
| Control | | 14.90 | — | 0/10 |

(3) An antitumor activity test using Meth-A in Balb/c mice 25 thousand Meth-A tumor cells were transplanted into the subcutaneous portion of the right inguinal part of Balb/c mice having a body weight of about 23 g, and then, the same operation as in (1) above was performed.

The results are shown in Table 3.

TABLE 3

| Sample | Dosage (mg/kg/day) | Average weight of tumor (g) | Tumor inhibition ratio (%) | Complete regression |
|---|---|---|---|---|
| Product of Example 1 | 1 | 7.74 | 42.1 | 0/10 |
| Product of Example 1 | 5 | 5.57 | 58.3 | 0/10 |
| Product of Example 1 | 20 | 9.25 | 30.8 | 0/10 |
| Product of Example 2 | 5 | 6.73 | 49.6 | 0/10 |
| Product of Example 4 | 5 | 7.99 | 40.2 | 0/10 |
| Product of Example 4 | 20 | 9.33 | 30.2 | 0/10 |
| Product of Example 6 | 1 | 5.37 | 59.8 | 0/10 |
| Product of Example 6 | 5 | 7.45 | 44.2 | 0/10 |
| Product of Example 6 | 20 | 8.52 | 36.2 | 0/10 |
| Control | — | 13.36 | — | 0/10 |

(4) An antitumor activity test using Sarcoma 180 in C3H/He mice

Six million Sarcoma 180 cells were transplanted into the subcutaneous portion of the right inguinal part of C3H/He mice having a body weight of about 23 g, and then, the same operation as in (1) above was performed.

The results are shown in Table 4.

TABLE 4

| Sample | Dosage (mg/kg/day) | Average weight of tumor (g) | Tumor inhibition ratio (%) | Complete regression |
|---|---|---|---|---|
| Product of Example 1 | 1 | 5.14 | 60.2 | 0/10 |
| Product of Example 1 | 5 | 2.14 | 83.4 | 6/10 |
| Product of Example 1 | 20 | 4.62 | 64.2 | 1/10 |
| Product of Example 2 | 5 | 3.50 | 72.9 | 4/10 |
| Product of Example 3 | 5 | 4.94 | 61.7 | 2/10 |
| Product of Example 4 | 1 | 5.62 | 56.5 | 0/10 |
| Product of Example 4 | 5 | 4.93 | 61.8 | 1/10 |
| Product of Example 6 | 1 | 4.08 | 68.4 | 3/10 |
| Product of Example 6 | 5 | 2.05 | 84.1 | 6/10 |
| Control | | 12.91 | — | 0/10 |

(5) An antitumor activity test using Sarcoma 180 in Balb/c mice

Six million Sarcoma 180 cells were transplanted into the subcutaneous portion of the right inguinal part of the Balb/c mice having a body weight of about 23 g, and then, the same operation as in (1) above was performed.

The results are shown in Table 5.

TABLE 5

| Sample | Dosage (mg/kg/day) | Average weight of tumor (g) | Tumor inhibition ratio (%) | Complete regression |
|---|---|---|---|---|
| Product of Example 1 | 1 | 0.08 | 97.8 | 9/10 |
| Product of Example 2 | 1 | 0.09 | 97.5 | 8/10 |
| Product of Example 3 | 1 | 0.10 | 97.3 | 8/10 |
| Product of Example 4 | 1 | 0 | 100 | 10/10 |
| Product of Example 4 | 5 | 0 | 100 | 10/10 |
| Control | | 3.65 | | 0/10 |

(6) An antitumor activity test using Sarcoma 180 in C57BL/6 mice

Six million Sarcoma 180 cells were transplanted into the subcutaneous portion of the right inguinal part of the C57BL/6 mice having a body weight of about 20 g, and then the same operation as in (1) above was performed.

The results are shown in Table 6.

TABLE 6

| Sample | Dosage (mg/kg/day) | Average weight of tumor (g) | Tumor inhibition ratio (%) | Complete regression |
|---|---|---|---|---|
| Product of Example 1 | 1 | 0.15 | 95.8 | 8/10 |
| Product of Example 2 | 1 | 0.21 | 94.1 | 8/10 |
| Product of Example 3 | 1 | 0.30 | 91.5 | 7/10 |
| Product of Example 4 | 1 | 0.13 | 96.4 | 9/10 |
| Product of Example 4 | 5 | 0.12 | 96.6 | 9/10 |
| Control | | 3.57 | | 9/10 |

(7) An antitumor activity test using Sarcoma 180 in ddY mice

Six million Sarcoma 180 cells were transplanted into the subcutaneous portion of the right inguinal part of ddY mice having a body weight of about 23 g, and then, the same operation as in (1) above was performed.

The results are shown in Table 7.

TABLE 7

| Sample | Dosage (mg/kg/day) | Average weight of tumor (g) | Tumor inhibition ratio (%) | Complete regression |
|---|---|---|---|---|
| Product of Example 1 | 1 | 0.39 | 96.5 | 7/10 |
| Product of Example 2 | 1 | 1.08 | 90.3 | 7/10 |
| Product of Example 3 | 1 | 1.17 | 89.5 | 6/10 |
| Product of Example 4 | 1 | 0.25 | 97.7 | 8/10 |
| Product of Example 4 | 5 | 0.54 | 95.2 | 8/10 |
| Control | | 11.10 | | 0/10 |

(8) An antitumor activity test using CCM-adenocarcinoma in ICR-JCL mice

Six million CCM-adenocarcinoma cells were transplanted into the subcutaneous portion of the right inguinal part of ICR-JCL mice having a body weight of about 23 g, and then the same operation as in (1) above was performed.

The results are shown in Table 8.

TABLE 8

| Sample | Dosage (mg/kg/day) | Average weight of tumor (g) | Tumor inhibition ratio (%) | Complete regression |
|---|---|---|---|---|
| Product of Example 1 | 1 | 0.52 | 95.7 | 7/10 |
| Product of Example 2 | 1 | 0.61 | 95.0 | 8/10 |
| Product of Example 3 | 1 | 0.14 | 98.9 | 8/10 |
| Product of Example 4 | 1 | 0 | 100 | 10/10 |
| Product of Example 4 | 5 | 0.23 | 98.1 | 8/10 |
| Control | | 12.23 | | 0/10 |

(9) An antitumor activity test using NTF-reticulum cell sarcoma in ICR-JCL mice

Six million NFT-reticulum cell sarcoma cells were transplanted into the subcutaneous portion of the right inguinal part of ICR-JCL mice having a body weight of about 23 g, and then, the same operation as in (1) above was performed.

The results are shown in Table 9.

TABLE 9

| Sample | Dosage (mg/kg/day) | Average weight of tumor (g) | Tumor inhibition ratio (%) | Complete regression |
|---|---|---|---|---|
| Product of Example 1 | 1 | 0.51 | 91.1 | 8/10 |
| Product of Example 2 | 1 | 0.37 | 93.6 | 8/10 |
| Product of Example 3 | 1 | 0.88 | 84.7 | 6/10 |
| Product of Example 4 | 1 | 0.67 | 88.3 | 8/10 |
| Product of Example 4 | 5 | 0.83 | 85.6 | 6/10 |
| Control | | 5.75 | | 0/10 |

It is seen from the results of these experiments that the β-1,3-glucanpolyol of this invention significantly inhibits growth of experimental tumors, and exhibits marked antitumor activity in the test systems described in (2) to (9) against which, it has been generally thought, conventional known antitumor polysaccharides are not significantly effective. This suggests the great advantage of the β-1,3-glucanpolyol in application.

Thus, the glucanpolyol of this invention can be used for treating malignant tumors such as Sarcoma 180, Ehrlich Carcinoma and NFT-reticulum cell sarcoma in mice.

The toxicity of the β-1,3-glucanpolyol of this invention is very low, and the $LD_{50}$ values of the products obtained in Examples 1, 4 and 5, for example, on ICR-JCL mice are as shown in Table 10.

TABLE 10

| | ($LD_{50}$ values in g/kg) | | |
|---|---|---|---|
| Sample | Oral administration | Intraperitoneal administration | Intravenous administration |
| Product of Example 1 | above 20 | above 2 | above 0.5 |
| Product of Example 4 | above 20 | above 5 | 1.5 |
| Product of Example 5 | above 20 | above 5 | above 2.0 |

It was confirmed that by the effect of ultrasonic treatment, the products of Examples 4 and 5 have lower toxicity.

Preferably, the pharmaceutical composition of this invention usually contains about 1 to about 90% by weight of the glucanpolyol of this invention based on the total weight of the composition. The content of the glucanpolyol can be varied depending upon the dosage form of the composition.

The glucanpolyol of this invention can be formulated into orally administrable forms such as powder, granules capsules, tablets, coated tablets, syrups and aqueous preparations, and parenterally administrable forms such as injecting preparations, in combination with a pharmaceutically acceptable carrier or diluent.

The carrier or diluent may, for example, be various liquid or solid carriers or diluents. Examples of the carriers are solid carriers or diluents such as calcium phosphate, calcium carbonate, glucose, lactose, sucrose, dextrin, sucrose esters, starch, sorbitol, mannitol, crystalline cellulose, talc, kaolin, synthetic aluminium silicate, carboxymethyl cellulose, methyl cellulose, cellulose acetate phthalate, sodium alginate, polyvinylpyrrolidone, polyvinyl alcohol, gum arabic, tragacanth gum, gelatin, agar flour and shellac; and liquid carriers or diluents such as water, physiological saline, ethanol, propylene glycol, polyethylene glycol, glycerin, Hartman liquid, and Ringer's liquid.

The glucanpolyol composition in accordance with this invention can be administered by general procedures known in treating tumors, for example by subcutaneous, intramuscular or intravenous injection, oral administration, intrarectal administration, coating as an external drug, and infusion. The dosage and administration schedule of the glucanpolyol may be properly selected in consideration of the types and conditions, etc. of the host and tumor.

For example, the dosage of the glucanpolyol of this invention in oral administration is usually 1 to 5000 mg/kg body/day, preferably 2 to 2000 mg/kg body/day, and in injection 0.5 to 5000 mg/kg body/day, preferably 1 to 2000 mg/kg body/day, more preferably 2 to 500 mg/kg body/day.

The glucanpolyol may be used in combination with other antitumor agents. A combination which will bring about an increase in immulological effect is especially effective.

The following Examples illustrate the present invention without any intention of limiting the invention thereby.

| Referential Example (production of the starting β-1,3-glucan) | |
|---|---|
| Glucose | 30 g |
| Polypeptone | 3 g |
| Yeast extract | 3 g |
| $K_2HPO_4$ | 1 g |
| $MgSO_4.7H_2O$ | 0.5 g |
| Water | 1 liter |
| pH 6.50 | |

One hundred milliliters of a liquid culture medium having the above composition was placed into each of 150 Sakaguchi flasks having a capacity of 500 ml, and each flask was sealed with a cotton stopper. The flasks were sterilized at 120° C. for 20 minutes, and a Pestalotia No. 815 strain separately cultivated in a slant culture medium was inoculated in each of these culture media in a customary manner and cultivated at 28° C. for 7 days while shaking at a rate of 120 times/min. with an amplitude of 7 cm to obtain 13.5 liters of a culture broth. To the culture broth was added 13.5 liters of distilled water, and the mixture was well stirred to make it uniform. It was then centrifuged for 30 minutes at 10,000 G to remove the mycelia. Thus, 21.5 liters of the supernatant liquid was obtained. Sixty liters of acetone was added to the supernatant liquid with stirring to form a precipitate. The precipitate was taken out, and washed with acetone twice and then dried to afford 52.5 g of a crude glucan.

EXAMPLE 1

Fifty grams of the fibrous glucan obtained in the Referential Example was cut to small pieces, and suspended in 16 liters of a 0.5% aqueous solution of sodium chloride. The mixture was stirred at about 40° C. for 3 hours, and pulverized and homogenized by a homogenizer at 15,000 rpm for 20 minutes. Furthermore, 16 liters of distilled water was added, and the mixture was fully stirred and centrifuged at 4,000 rpm for 30 minutes to obtain an insoluble matter. Twenty liters of distilled water was added to the resulting water-insoluble portion, and the mixture was fully stirred and similarly centrifuged. This operation was performed twice, and sodium hydroxide was added to the resulting water-insoluble portion so that the final concentration reached 0.5 N. The total volume of the mixture was adjusted to 15 liters, and it was stirred at room temperature for 2 hours to form a solution. The solution was centrifuged at 4,000 rpm for 30 minutes, and a small amount of the residue was removed. The supernatant liquid was neutralized with 6 N hydrochloric acid, and an equal volume of methanol was added. The mixture was centrifuged at a speed of 2,000 rpm for 5 minutes to form a precipitate. Water (10 liters) was added to the resulting precipitate, and the mixture was fully stirred, and then subjected to the same re-precipitating operation, and lyophilized to form 40 g of a glucan as a starting material.

Five grams of the starting glucan was suspended in 2 liters of an aqueous solution containing 6.65 g of sodium metaperiodate (NaIO$_4$), and the suspension was reacted with stirring at 10° C. for 7 days in a darkroom. Ethylene glycol (1.5 g) was added to the reaction mixture to decompose the excess of sodium metaperiodate. Then, a small amount of sodium bicarbonate was added to render the reaction solution weakly alkaline. Then, 1.2 g of sodium borohydride was added to perform reduction at room temperature for 2 days with stirring. After the reduction, the excess of sodium borohydride was decomposed (pH<6) with a suitable amount of acetic acid. The resulting product was dialyzed against flowing water for 2 days. The residual solution was filtered using a filtration assistant (celite). To the filtrate was added three times its volume of methanol to obtain a precipitate. Water was added to the precipitate, and the mixture was lyophilized to afford 3.1 g of β-1,3-glucanpolyol as a white fibrous substance.

The properties of the product were as follows:
[η]: 6.21
Elemental analysis: C=40.32%; H=6.00%
Proportion of side chains (A): 0
Proportion of side chains (B): 69.1

(The proportions of the side chains (A) and (B) are per 100 β-1,3-glucopyranose units of the main chain; the same basis applies to the subsequent Examples.)

EXAMPLE 2

Five grams of the starting glucan obtained in Example 1 was suspended in 1 liter of an aqueous solution containing 4.16 g of sodium metaperiodate, and the suspension was reacted at 10° C. for 5 days with stirring in a darkroom. After the reaction, the reaction solution was dialyzed against flowing water, and the residual solution was centrifuged at 4,000 rpm for 30 minutes. The resulting precipitate was suspended in 1 liter of water, and 880 mg of sodium borohydride was added. The reduction was performed at room temperature for 2 days with stirring. After the reducing reaction, the excess of sodium borohydride was decomposed by adding a suitable amount of acetic acid (pH<6.0). The product was centrifuged at 4,000 rpm for 30 minutes. Water (2 liters) was added to the precipitate, and after stirring, the mixture was centrifuged. The resulting supernatant liquid was combined with the supernatant liquid formed in the previous centrifugal operation, and to the solution was added 1.5 times its volume of methanol. The mixture was centrifuged at 2,000 rpm for 5 minutes to form a precipitate. The precipitate was dissolved in 1.5 liters of water, and the same re-precipitating operation using methanol was performed. The resulting precipitate was dehydrated with methanol, and dried under reduced pressure to afford 2.8 g of β-1,3-glucanpolyol as a white powder.

The properties of the product were as follows:
[η]: 7.25
Elemental analysis: C=40.39%; H=5.90%
Proportion of side chains (A): 27.8
Proportion of side chains (B): 41.7

EXAMPLE 3

The procedure of Example 2 was repeated except that 2.8 g of sodium metaperiodate and 590 mg of sodium borohydride were used. Thus, β-1,3-glucanpolyol was obtained as a white powder in an amount of 2.5 g.

The properties of the product were as follows:
[η]: 7.68
Elemental analysis: C=40.42%; H=5.88%;
Proportion of side chains (A): 41.3
Proportion of side chains (B): 28.7

EXAMPLE 4

Five grams of the starting glucan was oxidized with sodium metaperiodate and reduced with sodium borohydride in the same way as in Example 1. Then, the excess of sodium borohydride was decomposed by adding a suitable amount of acetic acid (pH=6.0), and the mixture was dialyzed against flowing water.

The residual non-dialyzed solution was diluted with water so that the sugar concentration became 0.25%. Thus, about 1250 ml of a solution was obtained. The solution was cooled to less than 5° C., and subjected to ultrasonic treatment for 100 minutes at an oscillating frequency of 20 KHz and an output of 60 W while maintaining it cool (30° C. at the highest). The treated solution was filtered using a filtration assistant (celite). The filtrate was concentrated under reduced pressure (to 500 ml), and 3 times its volume of acetone was added to form a precipitate.

The precipitate was dissolved in water, and lyophilized to afford 2.4 g of β-1,3-glucanpolyol as a white fibrous substance.

The properties of the product were as follows:
[η]: 3.27
Elemental analysis: C=40.51%; H=6.22%;
Proportion of side chains (A): 0
Proportion of side chains (B): 68.3

EXAMPLE 5

Five grams of the starting glucan was oxidized with sodium metaperiodate and then reduced with sodium borohydride in the same way as in Example 2. Then, the excess of sodium borohydride was decomposed with acetic acid (pH<6), and the product was dialyzed against flowing water. The residual solution was prepared to a sugar concentration of 0.25% to form 1250 ml of a solution. The solution was subjected to ultrasonic treatment for 200 minutes at an oscillating frequency of 20 KHz and an output of 70 W while maintaining it cool (35° C. at the highest). The treated solution was filtered using a filtration assistant (celite), and further filtered under pressure using a Millipore Filter having a pore size of 0.45 micron. The filtrate was concentrated under reduced pressure (to about 500 ml), and lyophilized to afford 2.9 g of β-1,3-glucanpolyol.

The properties of the product were as follows:
[η]: 1.87
Elemental analysis: C=40.48%; H=5.95%
Proportion of side chains (A): 27.0
Proportion of side chains (B): 40.2

EXAMPLE 6

Five grams of the starting glucan obtained in Example 1 was suspended in 2 liters of a 0.05 N acetate buffer (pH=5) containing 5.91 g of potassium metaperiodate dissolved therein, and the suspension was reacted at 10° C. for 10 days with stirring in a darkroom. Ethylene glycol (1.5 g) was added to the reaction solution, and the mixture was dialyzed against flowing water. A small amount of sodium bicarbonate was added to the residual solution to render it weakly alkaline. Then, 1.2 g of sodium borohydride was added, and the mixture was stirred at room temperature for 2 days to perform reduction. After the reduction, the excess of sodium borohydride was decomposed with a suitable amount of acetic acid, and the product was dialyzed against flowing water.

The residual non-dialyzed solution was concentrated under reduced pressure, and lyophilized to afford 3.4 g of β-1,3-glucanpolyol as a white fibrous substance.

The properties of the product were as follows:
[η]: 9.48
Elemental analysis: C=40.36%; H=5.92%
Proportion of side chains (A): 14.4
Proportion of side chains (B): 55.6

EXAMPLE 7

Five grams of the fibrous glucan obtained in Referential Example was suspended in 2.0 liters of water, and pulverized and homogenized by a homogenizer (15,000 rpm, 20 minutes). Then, 500 ml of an aqueous solution containing 6.65 g of sodium metaperiodate dissolved therein was added, and they were reacted at 15° C. for 7 days with stirring in a darkroom. After the reaction, the reaction mixture was reduced by the same operation as in Example 1. The excess of sodium borohydride was decomposed with acetic acid, and the product was dialyzed against flowing water. After the dialysis, the residual solution was centrifuged at 4,000 rpm for 30 minutes. Water (2 liters) was added to the precipitate, and after stirring, the mixture was centrifuged. The resulting supernatant liquid was combined with the supernatant liquid formed in the previous centrifugal operation, and to the solution was added 2 times its volume of acetone to form a precipitate. Water (1 liter) was added to the precipitate, and acetone was added to perform a re-precipitating operation in the same manner as above. The precipitate was dehydrated with methanol, and dried under reduced pressure to afford 2.4 g of β-1,3-glucanpolyol as a white powder.

The properties of the product were as follows:
[η]: 8.55
Elemental analysis: C=40.38%; H=6.05%
Proportion of side chains (A): 1.3
Proportion of side chains (B): 67.8

EXAMPLE 8

Preparation of pharmaceutical compositions:

Tablets

|  | Weight (mg) |
| --- | --- |
| Glucan polyol of Example 2 | 2000 |
| Lactose | 1400 |
| Polyvinyl pyrrolidone | 400 |
| Talc | 500 |
| Starch | 200 |

The glucanpolyol was mixed with lactose, and the mixture was passed through a US standard sieve (60 mesh). Then, the mixture was wetted with alcoholic polyvinyl pyrrolidone, and passed through a 12-mesh sieve to form granules which were then dried. The dried granules were passed through a 16-mesh sieve, and talc and starch were added. The mixture was tableted to form tablets.

Granules

|  | Weight (mg) |
| --- | --- |
| Glucanpolyol of Example 2 | 2000 |
| Methyl cellulose | 1500 |

-continued

|  | Weight (mg) |
| --- | --- |
| Corn starch | 800 |
| Polyvinylpyrrolidone | 200 |
| Perfume | some |

The glucanpolyol, methyl cellulose, perfume and corn starch were mixed, and passed through a 60-mesh sieve. The mixture was wetted with alcoholic polyvinylpyrrolidone, and granulated through a stainless steel sieve having a diameter of 0.7 mm.

Injecting preparation

|  | Weight (mg) |
| --- | --- |
| Glucanpolyol of Example 4 | 500 |
| Glucose | 2000 |
| Distilled water | moderate |

The glucanpolyol and glucose were dissolved in distilled water for injection to a volume of 50 ml, and then formed into an injecting preparation in a customary manner.

What we claim is:

1. β-1,3-glucanpolyol derived from β-1,3-glucan produced by a β-1,3-glucan-producing strain of the genus Pestalotia, said glucanpolyol having the following characteristics [I] and [II]:

[I] said glucanpolyol comprises a main chain having as repeating units β-1,3-glucopyranose units of the following formula wherein Glc represents a glucopyranose residual moiety, and bonded thereto, either side chains of formula (B), or both side chains of formulas (A) and (B) below wherein n represents a number of from 0 to 1, and ─→3) β-D-Glc (1→ represents the above main chain, wherein n and →3) β-D-Glc (1→ are the same as defined with respect to formula (A), and R represents a groups derived from β-D-glucopyranose of the formula said glucanpolyol has an intrinsic viscosity of about 1 to about 10 and wherein, per 100 β-1,3-glucopyranose units of the main chain, the number of said side chains of formula (B) is about 25 to about 70, and the number of said side chains of formula (A) is 0 to about 45.

* * * * * said glucanpolyol has an intrinsic viscosity of about 1 to about 10 and wherein, per 100 β-1,3-glucopyranose units of the main chain, the number of said side chains of formula (B) is about 25 to about 70, and the number of said side chains of formula (A) is 0 to about 45.

* * * * *